United States Patent
Gagnon et al.

(10) Patent No.: US 8,515,148 B2
(45) Date of Patent: Aug. 20, 2013

(54) GEOMETRICAL TRANSFORMATIONS PRESERVING LIST-MODE FORMAT

(75) Inventors: Daniel Gagnon, Twinsburg, OH (US); Patrick Olivier, Solon, OH (US); Parmeshwar Kishore Khurd, Shaker Heights, OH (US)

(73) Assignee: Koninklijke Philips N.V., Eindhoven (NL)

( * ) Notice: Subject to any disclaimer, the term of this patent is extended or adjusted under 35 U.S.C. 154(b) by 195 days.

(21) Appl. No.: 12/991,719

(22) PCT Filed: May 13, 2009

(86) PCT No.: PCT/IB2009/051987
§ 371 (c)(1),
(2), (4) Date: Nov. 9, 2010

(87) PCT Pub. No.: WO2009/144607
PCT Pub. Date: Dec. 3, 2009

(65) Prior Publication Data
US 2011/0064295 A1  Mar. 17, 2011

Related U.S. Application Data

(60) Provisional application No. 61/056,473, filed on May 28, 2008.

(51) Int. Cl.
*G06K 9/00* (2006.01)
(52) U.S. Cl.
USPC ......................................................... 382/131
(58) Field of Classification Search
None
See application file for complete search history.

(56) References Cited

U.S. PATENT DOCUMENTS

| | | | | |
|---|---|---|---|---|
| 6,980,683 | B2* | 12/2005 | Jones | 382/131 |
| 7,923,690 | B2* | 4/2011 | Thielemans | 250/363.03 |
| 7,929,690 | B2* | 4/2011 | Gisin et al. | 380/29 |
| 8,188,736 | B2* | 5/2012 | Schulz et al. | 324/309 |
| 8,193,815 | B2* | 6/2012 | Prescher et al. | 324/501 |

(Continued)

FOREIGN PATENT DOCUMENTS

| WO | 2006111883 A2 | 10/2006 |
|---|---|---|
| WO | 2006134332 A2 | 12/2006 |
| WO | 2007100955 A2 | 9/2007 |

OTHER PUBLICATIONS

Respiratory motion in positron emission tomography for oncology applications: Problems and solutions D. Visvikis, Oct. 2006.*
Chung, A. J., et al.; List-Mode Affine Rebinning for Respiratory Motion Correction in PET Cardiac Imaging; 2006; MIAR, LNCS; 4091; pp. 293-300.

(Continued)

*Primary Examiner* — Nancy Bitar

(57) ABSTRACT

A diagnostic imaging device includes detector elements (16) for detecting γ-rays indicative of nuclear decay events. The detected γ-rays are used to produce lines of response (LORs) (46), which are time stamped (20) and stored in list mode. The LORs are reconstructed (34) into an image. An image analysis processor (38) analyzes the image for motion artifacts and iteratively adjusts an event transform processor (30) to transform selected LORs to minimize the motion artifacts. If the transformed LOR (50) does not correspond with a pair of detector elements (16), closest detector elements (52, 54) are determined. Candidate LORs (62) are created between the closest and neighboring detector elements. An event location (40) on an LOR (46) is determined from the time-of-flight (TOF) information and then transformed (47) to generate a transformed event location (48). The candidate LOR (62) which most nearly intersects the transformed event location (40) and the appropriately updated TOF information is selected for use in image reconstruction.

4 Claims, 3 Drawing Sheets

(56) References Cited

U.S. PATENT DOCUMENTS

| | | | |
|---|---|---|---|
| 2004/0030246 A1* | 2/2004 | Townsend et al. | 600/427 |
| 2006/0140482 A1 | 6/2006 | Koehler | |
| 2006/0266947 A1 | 11/2006 | Krieg et al. | |
| 2009/0154641 A1* | 6/2009 | Thielemans | 378/21 |
| 2009/0250616 A1* | 10/2009 | Solf et al. | 250/363.04 |

OTHER PUBLICATIONS

Visvikis, D., et al.; Respiratory motion in positron emission tomography for oncology applications: Problems and solutions; 2006; Nuclear Instruments and Methods in Physics Research A; 569:453-457.

* cited by examiner

GEOMETRICAL TRANSFORMATIONS PRESERVING LIST-MODE FORMAT

CROSS REFERENCE TO RELATED APPLICATIONS

This application claims the benefit of U.S. provisional application Ser. No. 61/056,473 filed May 28, 2008, which is incorporated herein by reference.

The present application relates to the diagnostic imaging arts. It finds particular application in correcting for patient motion in a nuclear medicine scanner that utilizes list-mode data acquisition, and will be described with particular reference thereto. It is to be understood, however, that it also finds application in other devices that use a list-mode data acquisition, and is not necessarily limited to the aforementioned application.

Nuclear imaging devices, and particularly PET scanners are continuously acquiring data over a relatively long period of time. Over that period of time, movement typically occurs in the subject. Radiation events occurring in the moving parts of the subject are smeared over their motion trajectory. Typically, motion such as cardiac or respiratory motion is monitored with external devices. Based on the respiratory or cardiac state when data is received, the data is shifted in accordance with the anticipated internal motion. Shifting events to a common motion state includes the application of a geometrical transform of the spatial coordinates at which individual counts are received. However, the external monitoring does not always predict the actual internal motion states accurately.

Also, when the spatial coordinates of the events is shifted or transformed to compensate for motion, the shifted coordinates can fall between discrete detector elements. Discretizing the shifted coordinates to nearest real detector coordinates enables events with like coordinates to be binned for accelerated reconstruction. However, some loss of information generally occurs during the discretization of transformed events. This loss of information can hinder full compensation of motion blur in an eventual reconstruction.

The present application provides a new and improved event transformation that is able to preserve list-mode data which overcomes the above-referenced problems and others.

In accordance with one aspect, a diagnostic imaging apparatus is provided. A detector array including individual detectors receives radiation events from an imaging region. A triggering processor assigns a time stamp to received potential events. An event verification processor applies verification criteria to detector channel hits. An event transformation processor transforms received events and corresponding lines of response into spatially displaced transformed events. An event storage buffer stores valid time stamped events. A reconstruction processor reconstructs valid events into an image representation of the imaging region.

In accordance with another aspect, a method of diagnostic imaging is provided. Potential radiation events are received from an imaging region. A time stamp is assigned to received potential events. Verification criteria are applied to the potential events. Verified events and corresponding lines of response are transformed into spatially displaced transformed events. Valid time stamped events are stored. Valid events are reconstructed into an image representation of the imaging region.

In accordance with another aspect, a method of diagnostic imaging is provided. Time indexed data of radiation events is obtained. At least one geometrical transform is performed on data that is affected by motion to generate revised time indexed data. An image based on the revised time indexed data is reconstructed.

One advantage lies in the ability to correct for motion more accurately.

Another advantage resides in the ability to correct for motion without external monitors or improve the accuracy with which internal motion is determined using external monitors.

Another advantage lies in the ability to utilize time-of-flight information to assist in transforming an event.

Another advantage lies in the ability to utilize system response function to assist in transforming an event Another advantage lies in using standard reconstruction software by virtue of transferring an original list mode file into another, motion-corrected list mode file.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
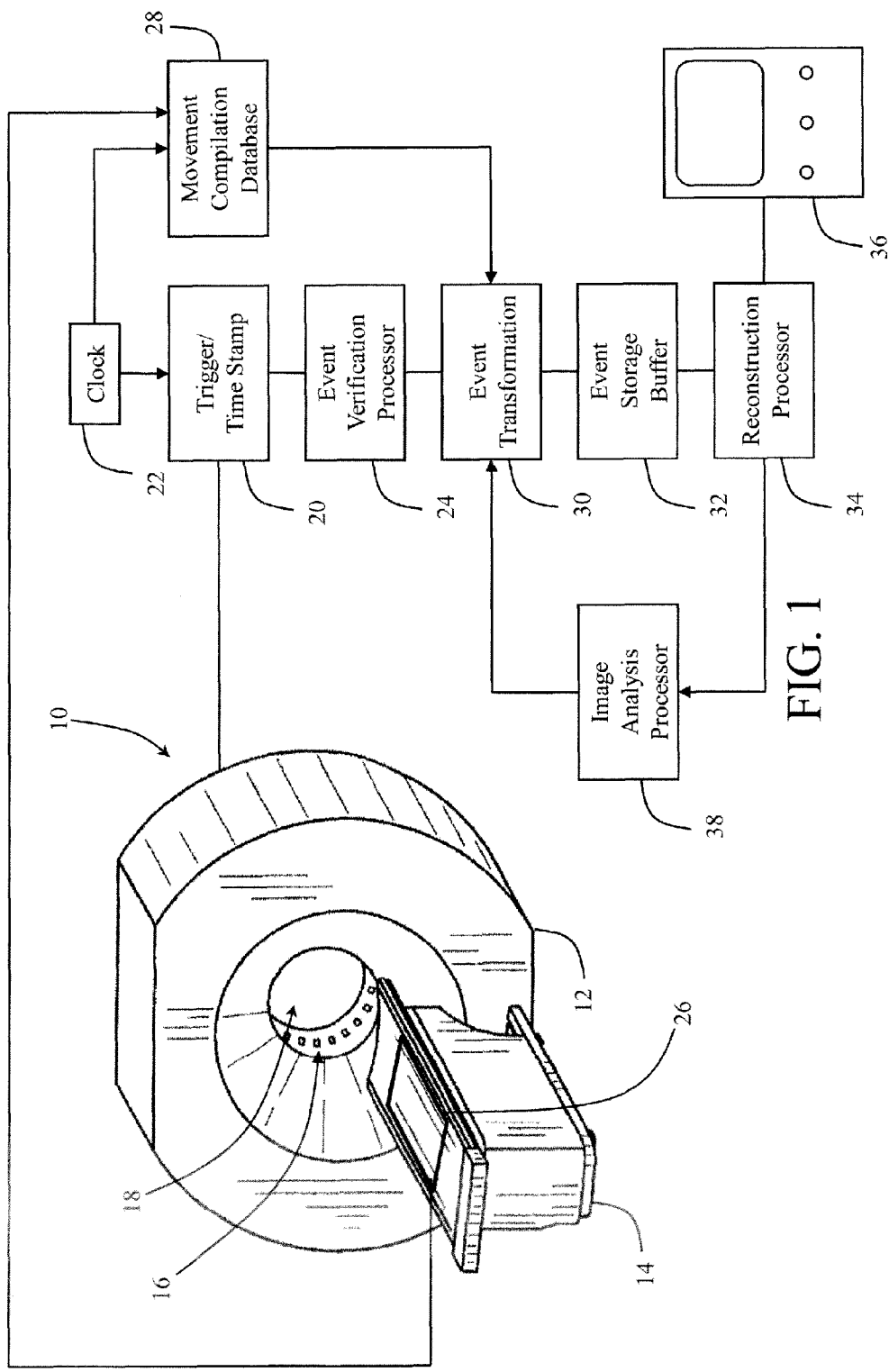
FIG. 1 is a diagrammatic illustration of a nuclear imaging device in accordance with the present application.

With reference to FIG. 1, a diagnostic imaging device 10 includes a housing 12 and a subject support 14. Enclosed within the housing 12 is a detector array. The detector array includes a plurality of individual detector elements 16. While one particular embodiment is described with reference to a positron emission tomography (PET) scanner, it is to be understood that the present application is also useful in astrophysics, such as in gamma ray telescopes, radiography, security, industrial, and other medical applications, such as single photon emission computed tomography (SPECT) and x-ray. Generally, the present application finds use in imaging x-rays, gamma rays, or other charged particles with high energy and spatial resolution. The array is arranged so that detector elements 16 are disposed adjacent an imaging region 18. The detector array can be a ring of detectors 16, multiple rings, one or more discrete flat or arced panels, or the like. In positron emission tomography (PET), a pair of gamma rays is produced by a positron annihilation event in the imaging region and travel in opposite directions. These gamma rays are detected as pairs, with a slight time difference (on the order of nanoseconds) between detections if one gamma ray travels farther to reach a detector than the other. Accordingly, in PET scanners, the detector arrays typically encircle the imaging region.

Before the PET scan commences, a subject is injected with a radiopharmaceutical. In one common exam, the radiopharmaceutical contains a radioactive element coupled to a tag molecule. The tag molecule is associated with the region to be imaged, and tends to gather there through normal body or metabolic processes. For example, rapidly multiplying cancer cells tend to expend abnormally high amounts of energy duplicating themselves. The radiopharmaceutical can be linked to a molecule, such as glucose, that a cell typically metabolizes to create energy causing the radiopharmaceutical to gather in such regions and appear as "hot spots" in the image. The rate at which the radiopharmaceutical is absorbed (uptake) and the rate at which the glucose is metabolized and the radioisotope is excreted as waste (washout) also has diagnostic value. Other techniques monitor tagged molecules flowing in the circulatory system. Radiopharmaceuticals linked to iodine selectively absorb in the thyroid. Other molecules are absorbed in other organs or tissues.

When a gamma ray strikes the detector array, the location of the struck detector element and the strike time are recorded. A triggering processor 20 monitors each detector 16 for an energy spike, e.g., integrated area under the pulse, characteristic of the energy of the gamma rays generated by the radiopharmaceutical. The triggering processor 20 checks a clock 22 and stamps each detected gamma ray with a time of leading edge receipt stamp. In PET imaging, the time stamp, energy estimate and position estimation are first used by an event verification processor 24 to determine whether there is a coincident event. Accepted pairs of coincident events define lines of response (LORs). Because gamma rays travel at the speed of light, if detected gamma rays arrive more than several nanoseconds apart, they probably were not generated by the same annihilation event and are discarded. Timing is especially important in time of flight PET (TOF-PET), as the minute difference in substantially simultaneous coincident events can be used to further localize the annihilation event along the LOR. As the temporal resolution of events becomes more precise, the higher the accuracy with which an event can be localized along its LOR.

In one embodiment, the subject support 14, in addition to supporting a subject, also supports at least one movement sensor 26. The movement sensors 26 allow local motion to be detected and corrected. Any of several types of movement sensors 26 are contemplated. The movement sensors 26 record movement of the subject and report the states of movement to a movement compilation database 28. The movement compilation database checks the clock 22 and correlates the detection time and the motion state. The movement may be single events, such as when a patient voluntarily moves or shifts in the imaging region. It could also be periodic, such as movement related to heartbeat or breathing. Breathing induces local motion of the lung nodules and the neighboring tissue. Compensating for this local motion leads to better standard uptake values. Additionally, the motion of the lungs could be mapped across the breathing cycle. With cardiac motion, compensation can be made for the movement of the heart leading to improved detection of anomalies.

In one embodiment, the sensors 26 report the extent of the movement and what region or regions of the subject are affected by the movement. ECG or pulse sensors can be used to monitor motion related to the subject's heartbeat. Mechanical or ultrasonic monitors to measure air flow into and out of the lungs, mechanical or video monitors to measure chest expansion during breathing, or other respiratory sensors can be used to monitor the extent and timing of the subject's breathing. Voluntary movement may be monitored by external motion sensors, laser alignment devices, video cameras, or the like.

Although correcting for motion originating from the subject is one application, other applications are also possible. For instance, a user could perform a multi-modality image registration by operating on the list mode data. Another application includes multi-subject registration for different body parts. A user could register 4D cardiac data sets of individual subjects to a common 4D template. The motion of a radiopharmaceutical can be tracked based on a known model. Also, the system can correct for camera wobble in SPECT imaging. Certainly other applications are also possible.

Once an event pair is verified by the event verification processor 24, the LOR is passed to an event transformation processor 30 that checks the movement compilation database 28 to see in which motion state the event occurred. The event transformation processor 30 transforms the LOR from the detector coordinates of actual receipt to a transformed position where the pair of LOR defining events would have been received in a selected state of movement, e.g., a rest state.

LORs (both transformed and untransformed) with their time stamps are stored in an event storage buffer 32, and a reconstruction processor 34 reconstructs the LORs into an image representation of the subject using any appropriate reconstruction algorithm. The reconstruction can then be displayed for a user on a display device 36, printed, saved for later use, and the like.

In one embodiment, event data is collected in a "list-mode" format. Recording the relevant properties (detector coordinates, time stamp, etc.) of each detected event in a list has become a common practice in emission tomography applications and has become known as list-mode data acquisition and storage. The list-mode reconstruction approach differs in several ways from real time methods in which each LOR is backprojected or otherwise used in the reconstruction in the order received and discarded. List-mode data acquisitions provide extremely high temporal resolution with full spatial resolution, allowing frame durations to be determined after acquisition. When acquiring the data in list-mode format, the detector locations for each event can be stored to a high degree of accuracy with greater efficiency than achievable with frame mode acquisition. Gantry angles do not have to be binned into predefined frames, but can be recorded as the actual angle, thereby removing the impact of angular blurring with continuous acquisition. The actual energy of the interaction can be recorded instead of attributing the event's energy to one of a limited number of pre-defined windows. When increasing the dimensionality in this way, the data is not binned into a matrix, but is instead stored in a list and can be arranged and sorted by different parameters, e.g. time of receipt. List-mode can also store gating signals without temporal framing of the data before this information is completely available. The result is a significant increase in the fidelity of recording the projection data with list-mode acquisition, without a tremendous increase in storage space. Another advantage is the ability to identify events by the time of their occurrence, and beneficially to the present application, being able to associate that time with a movement event.

As previously mentioned, the event transformation processor 30 checks to see if any of the events are affected by an instance of movement. If a radiation event and the selected motion state temporally coincide, then the event transformation processor 30 transforms the LOR associated with the event to compensate for the recorded movement. The present application preserves list-mode data. In one embodiment, the list-mode data is collected and reconstructed into an image that contains the motion artifacts. The image is analyzed by an image analysis processor 38. The list-mode data that is affected by the movement is identified and transformed by the event transformation processor 30. The updated, transformed, events replace the old events in the event storage buffer 32. The reconstruction processor 34 then produces another, updated image. This process can be repeated iteratively until the motion artifacts are minimized or until an acceptable level of motion artifacts is attained.

Various image analysis techniques are contemplated. For example, predicted motion periodically can be used to select candidate LORs to check for potential transformation. The nature of the artifact can be analyzed to determine candidate LORs. Candidate LORs, random LORs, or systematically selected LORs can be removed from the reconstruction to determine if instances of artifacts decrease. Once an LOR which causes artifacts is identified, it is subject to a transform that is iteratively adjusted to minimize the artifacts. Numerous other image analysis techniques are also contemplated.

In another embodiment, motion is measured and the motion state is correlated to each LOR by the movement compilation database 28 prior to reconstruction. This takes advantage of the ability of the list-mode reconstruction technique of time stamping each individual event. In instances where a motion model can be estimated prior to reconstruction, such as when monitoring an ECG signal and the motion of the heart, the event LORs are initially transformed before reconstruction. In this manner, the reconstruction proceeds with LORs positionally transformed into the selected motion state. Of course, images based on such estimated models are still subject to motion artifacts. Accordingly, the reconstructed image is still analyzed by the image analysis processor 38 to adjust the applied transforms to remove such motion artifacts.

Figure 2:
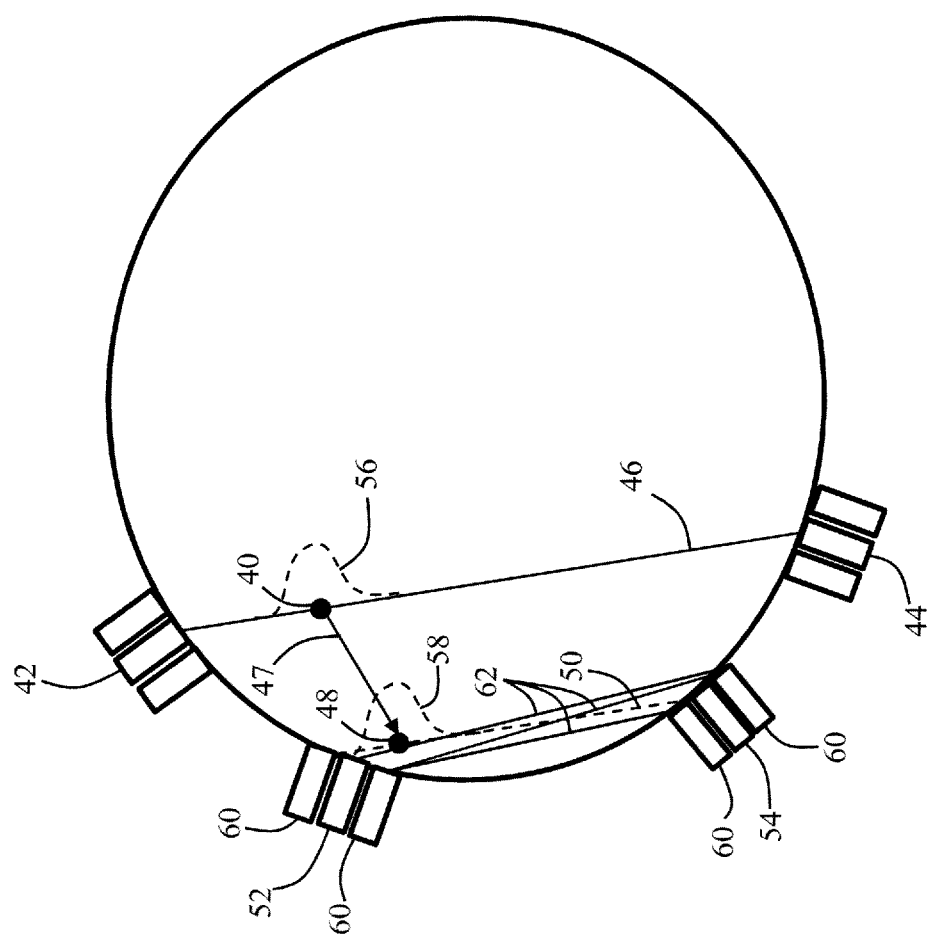
FIG. 2 is a cut-away view of the bore showing a transformed event and corresponding candidate LORs.

With reference now to FIG. 2, and continuing reference to FIG. 1, a transformation of an event LOR is described. Paired γ-rays are detected from event 40 at detectors 42 and 44, forming an initial LOR 46. After the event is time stamped and verified, the event transformation processor 30 is informed by the movement compilation database 28 and/or the image analysis processor 38 whether the event 40 coincides with movement. If it does, the event transformation processor 30 moves the event with a transform 47, to a transformed event location 48 corresponding to the selected motion state, defining a transformed LOR 50 (dotted line in FIG. 2).

A problem that often occurs, as is illustrated in FIG. 2, is that the transformed LOR 50 may not align with geometric centers of a new pair of detector elements. One way of proceeding with the transform, while preserving the integrity of the list-mode data, is to use detector elements 52, 54 that are nearest to the transformed LOR 50. This method can be used for both time-of-flight (TOF) and non-TOF list-mode acquisitions.

If TOF information is available, an improvement to the above-described nearest detector method is contemplated. When the ends of the transformed LOR 50 do not terminate exactly on detector geometric centers, the TOF information is used to identify the emission point along the LOR 46 of the event as received, and transformed into an emission point along the transformed LOR 48. That is, a location histogram 56 for the event 40 as received can be transformed into a location histogram 58 for the transformed event 48.

Next, detector centers (i.e., detectors 52 and 54) that are closest to the transformed LOR 50 are identified, and closest neighbor detectors 60 (both circumferentially and longitudinally) are also identified. Discrete LORs 62 that correspond to the closest detectors 52, 54 and the closest neighbor detectors 60 are calculated. From this collection of candidate discrete LORs 62, the LOR that most closely intersects the transformed emission point 48 is selected. Once the closest candidate transformed LOR 62 is selected, it is stored in the event storage buffer and used for reconstruction at the appropriate time.

Figure 3:
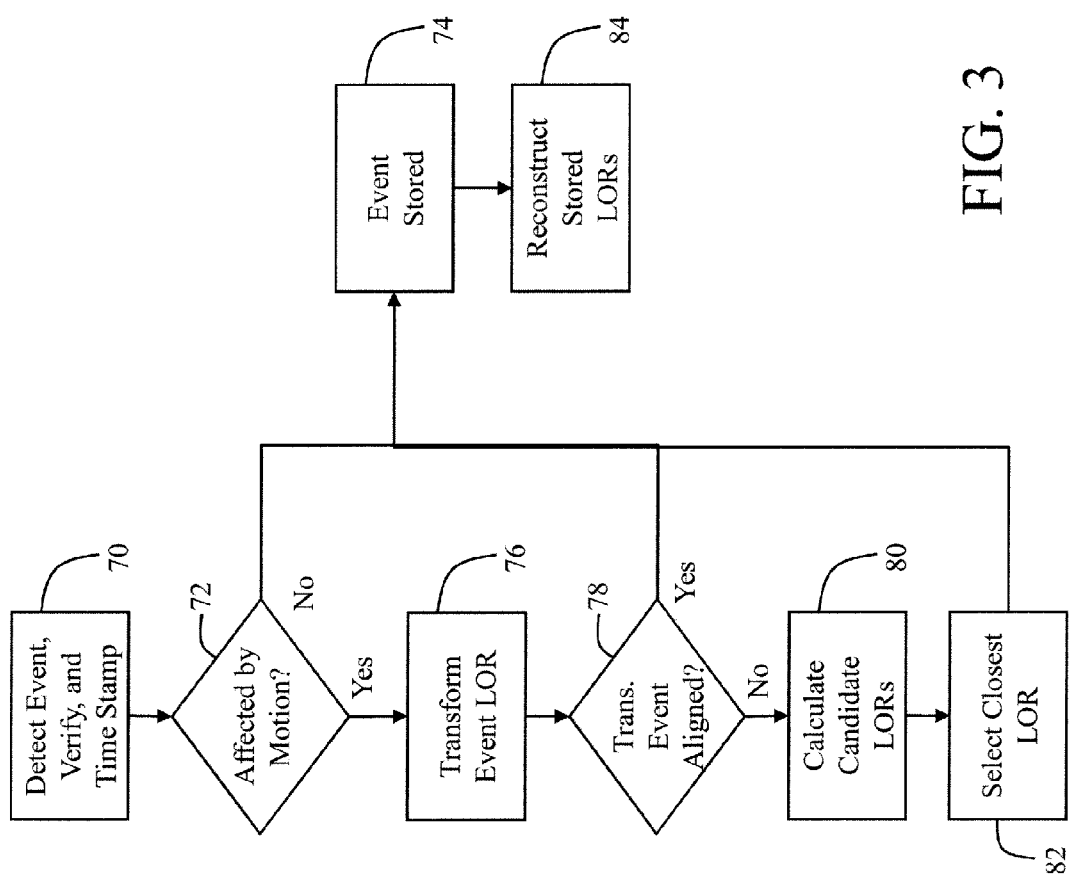
FIG. 3 is a flowchart illustrating a possible embodiment in accordance with the present application.

In one embodiment, a method is now described in reference to the flowchart of FIG. 3. In step 70, an event is detected as a pair of γ-rays, verified and time stamped. In step 72, the time and region of the event is checked against motion detection to see whether the event was affected by motion. If the event was not affected by motion, then it is passed as received to storage for later reconstruction in step 74.

If the event was affected by motion, a transform describing the motion is applied to the event in step 76. This shifts the LOR as received to a transformed LOR that compensates for the motion. The transformed LOR is checked to see if it does not line up with new crystal centers 78. In the event that the transformed LOR does not align with new crystal centers, candidate LORs are created in step 80 that connect the nearest crystals to the transformed LOR and their neighbors to each other. In the event that the transformed LOR lines up with new crystal centers, the transformed event is stored 74. Once candidate LORs are created, the candidate LOR that is closest to the event location as transformed is selected in step 82 and stored 74. The TOF for the transformed event is also appropriately updated. The TOF information is updated by calculating the distances of the transformed event location 48 to each of the two transformed crystals 52, 54, and computing the difference between those two distances. The result is then divided by the speed of light and quantized to fit into the appropriate frame of reference. Once all events have been processed in this manner, an appropriate reconstruction 84 is applied.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging apparatus, comprising:
a detector array including individual detectors for receiving radiation events from an imaging region;
a triggering processor for assigning a time stamp to received potential events;
an event verification processor that applies verification criteria to detector channel hits, wherein each verified radiation event is identified by a corresponding line of response;
an event transformation processor that:
transforms received events and corresponding lines of response into spatially displaced transformed events,
transforms the line of response as received into a transformed line of response,
identifies closest detector elements that are closest to endpoints of the transformed line of response,
identifies neighboring detector elements to the closest detector elements, and
creates a plurality of candidate lines of response that connect the closest detectors and the neighboring detectors;
a list mode event storage buffer for storing valid time stamped events; and
a reconstruction processor for reconstructing valid events into an image representation of the imaging region;
wherein the triggering processor generates time-of-flight information corresponding to each line of response, the event transformation processor transforming an event location derived from the time-of-flight information to create a transformed event location along the transformed line of response.

2. A diagnostic imaging apparatus, comprising:
a detector array including individual detectors for receiving radiation events from an imaging region;
an event verification processor that applies verification criteria to the potential events to identify pairs of detectors that define a corresponding line of response;

a triggering processor programmed to generate time-of-flight information including an estimated event location along the line of response;
an event transformation processor programmed to:
spatially displace the line of response in accordance with patient motion to define displaced ends of the line of response,
transform the event location from the time-of-flight information to create a transformed event location along the transformed line of response,
identify neighboring detector elements closest to the spatially displaced ends of the lines of response,
create a plurality of candidate lines of response that connect the spatially displaced ends of the lines of response and the neighboring detector elements;
select one of the plurality of candidate lines of response that runs closest to the transformed event location, and
update the time-of-flight information to correspond to the selected candidate line of response.

3. A method of diagnostic imaging, comprising:
detecting potential radiation events from an imaging region with detectors;
assigning a time index to the detected potential radiation events;
applying verification criteria to detected timed indexed potential events to identify pairs of detectors which define time indexed lines of response;
deriving event locations along corresponding time indexed lines of response from time-of-flight information;
applying a transform to transform the time indexed lines of response to a selected motion state and transform the event locations to transformed event locations;
identifying closest detector elements that are closest to endpoints of the timed indexed transformed lines of response and neighboring detector elements that neighbor the closest detector elements;
creating a plurality of candidate lines of response that connect the closest detector elements and the neighboring detector elements;
selecting one of the plurality of candidate lines of response that runs closest to the transformed event locations;
reconstructing the selected candidate lines of response into an image representation of the imaging region in the selected motion state; and
iteratively analyzing the reconstructed image representations for motion artifacts, adjusting the transforms applied to some of the lines of response, and reconstructing the lines of response transformed with the adjusted transforms, to reduce the motion artifacts.

4. A method of diagnostic imaging, comprising:
obtaining time indexed data of radiation events;
detecting motion of a subject based on a compilation of the time indexed data;
applying verification criteria to the time-indexed event data to identify pairs of detectors which define time indexed lines of response;
deriving event location data along the time indexed lines of response from time-of-flight information;
applying a transform to transform the time indexed lines of response to a selected motion state and to transform the event locations to transformed event locations;
identifying closest detector elements that are closest to endpoints of the transformed time indexed lines of response and neighboring detector elements that neighbor the closest detector elements;
creating plurality of candidate time-indexed lines of response that connect the closest detector elements and the neighboring detector elements;
selecting one of the plurality of candidate time-indexed lines of response that runs closest to the transformed event location data;
reconstructing the selected candidate time-indexed lines of response into an image in the selected motion state.

\* \* \* \* \*